United States Patent [19]

Haynor et al.

[11] Patent Number: 5,879,297
[45] Date of Patent: Mar. 9, 1999

[54] SYSTEM AND METHOD TO DETERMINE THE LOCATION AND ORIENTATION OF AN INDWELLING MEDICAL DEVICE

[75] Inventors: David R. Haynor, Seattle; Christopher P. Somogyi, Woodinville; Robert N. Golden, Kirkland, all of Wash.

[73] Assignee: Lucent Medical Systems, Inc., Bellevue, Wash.

[21] Appl. No.: 852,940

[22] Filed: May 8, 1997

[51] Int. Cl.⁶ ................................................. A61B 5/00
[52] U.S. Cl. ..................... 600/407; 128/899; 600/409; 600/424
[58] Field of Search ................. 600/407, 409, 600/431, 433, 424; 128/899

[56] References Cited

U.S. PATENT DOCUMENTS

| | | | |
|---|---|---|---|
| 3,757,773 | 9/1973 | Kolin | 128/2.05 F |
| 4,063,561 | 12/1977 | McKenna | 128/351 |
| 4,244,362 | 1/1981 | Anderson | 128/200.26 |
| 4,249,536 | 2/1981 | Vega | 128/349 |
| 4,317,078 | 2/1982 | Weed et al. | 324/208 |
| 4,402,310 | 9/1983 | Kimura | 128/4 |
| 4,608,992 | 9/1986 | Hakim et al. | 128/654 |
| 4,619,247 | 10/1986 | Inoue et al. | 128/6 |
| 4,671,287 | 6/1987 | Fiddian-Green | 128/631 |

(List continued on next page.)

FOREIGN PATENT DOCUMENTS

| | | |
|---|---|---|
| 0302001A1 | 7/1988 | European Pat. Off. . |
| 2903357A1 | 7/1980 | Germany . |
| 4014947A1 | 11/1991 | Germany . |
| 9608999 A1 | 3/1996 | WIPO . |

OTHER PUBLICATIONS

James, "Duodenal Intubation with Magnet–Tipped Tubes," *The Lancet*, Jan. 27, 1951, pp. 209–210.

Wenger et al., "Magnet–Tipped Tubes for Studies of the Stomach and Duodenum," *Digestive Diseases* 15:383–393, 1970.

Gaston et al., "Experimental Studies in Dogs and Prospects of Application," *Journal of Neuroradiology* 15(2):137–147, 1988.

Ram and Meyer, "Heart Catheterization in a Neonate by Interacting Magnetic Fields: A New and Simple Method of Catheter Guidance," *Catheterization and Cardiovascular Diagnosis* 22:317–319 (1991).

(List continued on next page.)

*Primary Examiner*—Marvin M. Lateef
*Assistant Examiner*—Shawna J. Shaw
*Attorney, Agent, or Firm*—Seed and Berry LLP

[57] ABSTRACT

A device to detect the location of a magnet coupled to an indwelling medical device within a patient uses three or more sets of magnetic sensors each having sensor elements arranged in a known fashion. Each sensor element senses the magnetic field strength generated by the magnet and provides data indicative of the direction of the magnet in a three-dimensional space. The device uses fundamental equations for electricity and magnetism that relate measured magnetic field strength and magnetic field gradient to the location and strength of a magnetic dipole. The device uses an iterative process to determine the actual location and orientation of the magnet. An initial estimate of the location and orientation of the magnet results in the generation of predicted magnetic field values. The predicted magnetic field values are compared with the actual measured values provided by the magnetic sensors. Based on the difference between the predicted values and the measured values, the device estimates a new location of the magnet and calculates new predicted magnetic field strength values. This iteration process continues until the predicted values match the measured values within a desired degree of tolerance. At that point, the estimated location matches the actual location within a predetermined degree of tolerance. A two-dimensional display provides an indication of the location of the magnet with respect to the housing of the detector. A depth indicator portion of the display can be used to provide a relative or absolute indication of the depth of the magnet within the patient.

30 Claims, 8 Drawing Sheets

U.S. PATENT DOCUMENTS

| | | | |
|---|---|---|---|
| 4,790,809 | 12/1988 | Kuntz | 604/8 |
| 4,809,713 | 3/1989 | Grayzel | 128/785 |
| 4,913,139 | 4/1990 | Ballew | 128/200.11 |
| 4,943,770 | 7/1990 | Ashley-Rollman et al. | 324/207.17 |
| 5,005,592 | 4/1991 | Cartmell | 128/899 |
| 5,042,486 | 8/1991 | Pfeilier et al. . | |
| 5,099,845 | 3/1992 | Besz et al. . | |
| 5,134,370 | 7/1992 | Jefferts et al. | 324/247 |
| 5,257,636 | 11/1993 | White | 128/897 |
| 5,325,873 | 7/1994 | Hirschi et al. | 128/899 |
| 5,377,678 | 1/1995 | Dumoulin et al. . | |
| 5,381,095 | 1/1995 | Andrews | 324/326 |
| 5,425,367 | 6/1995 | Shapiro et al. . | |
| 5,425,382 | 6/1995 | Golden et al. . | |
| 5,429,132 | 7/1995 | Guy et al. . | |
| 5,456,718 | 10/1995 | Szymaitis . | |
| 5,558,091 | 9/1996 | Acker et al. . | |
| 5,622,169 | 4/1997 | Golden et al. | 128/653.1 |
| 5,645,065 | 7/1997 | Shapiro et al. . | |

OTHER PUBLICATIONS

Williams et al. Abstract, "The Localisation of Enternal Tubes Using a Novel Non–Radiological Technique," *British Society of Gastroenterology* (Mar. 1992).

W. Weitschies, J. Wedemeyer, R. Stehr, and L. Trahms, "Magnetic Markers as a Noninvasive Tool to Monitor Gastrointestinal Transit," *IEEE Transactions on Biomedical Engineering, vol. 41, No. 2*, pp. 192–195, Feb. 1994.

SYSTEM AND METHOD TO DETERMINE THE LOCATION AND ORIENTATION OF AN INDWELLING MEDICAL DEVICE

TECHNICAL FIELD

This invention is generally directed to a system and method for detecting the location of an indwelling medical device within the body of a patient and, more specifically, to a detection apparatus which senses magnetic field strength generated by a magnet associated with the indwelling medical device.

BACKGROUND OF THE INVENTION

There are many instances in clinical medicine where detecting the location of a medical tube within a patient is important. For example, when positioning feeding tubes through the mouth or nose of a patient, it is essential that the end of the feeding tube pass into the patient's stomach, and that it does not "curl up" and remain in the esophagus. If the end of the feeding tube is not properly positioned within the stomach, aspiration of the feeding solution into the patient's lungs may occur. In addition to feeding tubes, a variety of other medical tubes require accurate positioning within a patient's body, including dilating tubes to widen an esophageal stricture, tubes for measuring pressure waves in the stomach and esophagus of a patient who is suspected of having esophageal motor disorders, Sengstaken-Blakemore tubes in the stomach and esophagus of a patient to control bleeding from varicose veins in the esophagus, colonic decompression tubes in the colon of a patient to assist in relieving distention of the colon by gas, urologic tubes in the bladder, ureter or kidney of a patient, and vascular tubes in the heart or pulmonary arteries of a patient.

Currently, the location of a medical tube within the body of a patient is routinely detected by the use of imaging equipment, such as a chest or abdominal X-ray. However, such a procedure requires transportation of the patient to an X-ray facility or, conversely, transportation of the X-ray equipment to the patient. This is both inconvenient and costly to the patient, and is particularly stressful in those instances where the patient repeatedly and inadvertently removes a medical tube, such as a feeding tube, thus requiring repeated reinsertion and X-rays.

Prior attempts at detecting the location of medical tubes within a patient have met with only limited success. For example, in U.S. Pat. No. 5,099,845 to Besz et al., a transmitter is located within a catheter, and an external receiver, tuned to the frequency of the transmitter, is used to detect the location of the catheter within the patient. This approach, however, requires either an external or internal power source to drive the transmitter. An external power source adds significant risk associated with shock or electrocution, and requires that electrical connections be made prior to positioning of the catheter within the patient. An internal power source, such as a battery, must be relatively small and can only provide power to the transmitter for a limited time. This precludes long-term detection of the catheter's location, and poses additional risks associated with placing a battery internally in a patient, such as the risk of battery leakage or rupture. In addition, the transmitter is relatively complex, and requires an active electronic circuit (either internal or external to the catheter), as well as the various wires and connections necessary for its proper function. Lastly, the signal produced by the transmitter is attenuated differently by different body tissues and bone. This attenuation requires adjustments in the transmitter's signal strength and frequency depending on the location of the catheter within the patient's body.

A further attempt at detecting the location of medical tubes within a patient is disclosed in U.S. Pat. No. 4,809,713 to Grayzel. There, an electrical cardiac-pacing catheter is held in place against the inner heart wall of a patient by the attraction between a small magnet located in the tip of the pacing catheter and a large magnet located on (e.g., sewn into) the patient's chest wall. An indexed, gimbaled, three-dimensional compass is used to determine the best location for the large magnet. The compass' operation relies upon the torque generated by the magnetic forces between the small magnet and the magnetized compass pointer in order to point the compass towards the small magnet. However, this compass will simultaneously try to orient itself to the earth's ambient magnetic field. Because of this, the forces between the small magnet and the magnetized compass pointer at distances greater than several centimeters are not strong enough to accurately orient the compass towards the small magnet. Furthermore, although the compass aids positioning of the large magnet, positioning of the small magnet, and hence the pacing catheter, still requires the use of imaging equipment, such as X-ray or ultrasound.

For the foregoing reasons, there is a need in the art for a medical tube, apparatus and method for detecting the location of the medical tube within the body of a patient which avoids the problems inherent in existing techniques. The medical tube, apparatus and method should provide for the detection of the medical tube at distances ranging from several centimeters to several decimeters, should not require the medical tube to have an internal or external power source, and should obviate the need to independently verify positioning of the medical tube with imaging equipment.

SUMMARY OF THE INVENTION

The present invention is embodied in a system and method for the detection of a position of a magnet associated with an indwelling medical device. The system includes a plurality of magnetic sensors that each generate a set of electrical signals as a function of the magnetic field strength generated from the magnet and a direction from the sensor to the magnet. A processor calculates a predicted position of the magnet in a 3-dimensional space and calculates a predicted value related to magnetic field strength of the magnet at the predicted location. The processor calculates a measured value related to the magnetic field strength of the magnet and determines the location of the magnet in the 3-dimensional space based on the difference between the predicted value and the measured value. In one embodiment, the processor performs an iterative process of calculating the predicted position and predicted value related to the magnetic field and alters the predicted position based on the difference between the predicted value and the measured value. The iterative process continues until the predicted value and the measured value match each other within a predetermined tolerance. The system also includes a display to provide a visual display of data related to the position of the magnet in the 3-dimensional space.

In one embodiment, the display is a two-dimensional display indicating the position of the magnet with respect to the housing. A depth indicator portion of the two-dimensional display provides an indication of the distance of the magnet from the housing. The display can include a visual indicator to assist the care giver in centering the housing over the magnet. The sensors themselves can be selected from a group of magnetic sensors comprising Hall-effect sensors, flux-gate sensors, wound-core inductive sensors, squid sensors, magneto-resistive sensors, and nuclear precession sensors.

The magnet has a magnetic dipole moment indicative of the orientation of the magnet. The sensors can detect the magnetic dipole moment and provide a visual indication on the display to indicate the magnet orientation.

In one embodiment, each sensor comprises first, second, and third sensor elements arranged in an orthogonal fashion to detect magnetic field strength in three dimensions corresponding to the first, second, and third orthogonally arranged sensor elements.

DETAILED DESCRIPTION OF THE INVENTION

The present invention provides a medical tube, apparatus and method for detecting the location of the medical tube within the body of a patient. As used herein, the term "medical tube" means any type of tube or device which may be inserted into a patient's body, including (but not limited to) catheters, guide wires, and medical instruments. For example, catheters include such items as feeding tubes, urinary catheters, guide wires and dilating catheters, as well as nasogastric tubes, endotracheal tubes, stomach pump tubes, wound drain tubes, rectal tubes, vascular tubes, Sengstaken-Blakemore tubes, colonic decompression tubes, pH catheters, motility catheters, and urological tubes. Guide wires are often used to guide or place dilators and other medical tubes. Medical instruments include endoscopes and colonoscopes. In short, the location of any foreign object within a patient's body is a suitable device for detection by the present invention, and is encompassed within the term "medical tube."

The present invention detects the location of the medical tube by sensing the magnetic field produced by a permanent magnet associated with the medical tube. As used herein, the term "associated with" means permanently fixed, removably attached, or in close proximity to, the medical tube. In one embodiment, such as a feeding tube, the magnet is associated with the end of the medical tube. In another embodiment, such as a Sengstaken-Blakemore tube, the magnet is associated with the medical tube at a location above the gastric balloon. Preferably, the magnet is a small, cylindrical, rotatably attached, rare-earth magnet. Suitable magnets include rare earth magnets such as samarium cobalt and neodymium iron boron, both of which generate high field strengths per unit volume. While magnets which generate a high field strength for their size are preferred, weaker magnets such as Alnico or ceramic may also be utilized.

Since the magnet is permanent, it requires no power source. Accordingly, the magnet maintains its magnetic field indefinitely, which allows long-term positioning and detection of medical tubes without the disadvantages associated with an internal or external power source. In particular, by avoiding the use of a power source, the undesirable electrical connections necessary for the use of a power source are avoided. Thus, there is no risk of electric shock to (or possible electrocution of) the patient. Furthermore, the magnet's static magnetic field passes unattenuated through body tissue and bone. This property allows the use of the present invention to detect the medical tube at any location within the patient's body.

Figure 1:
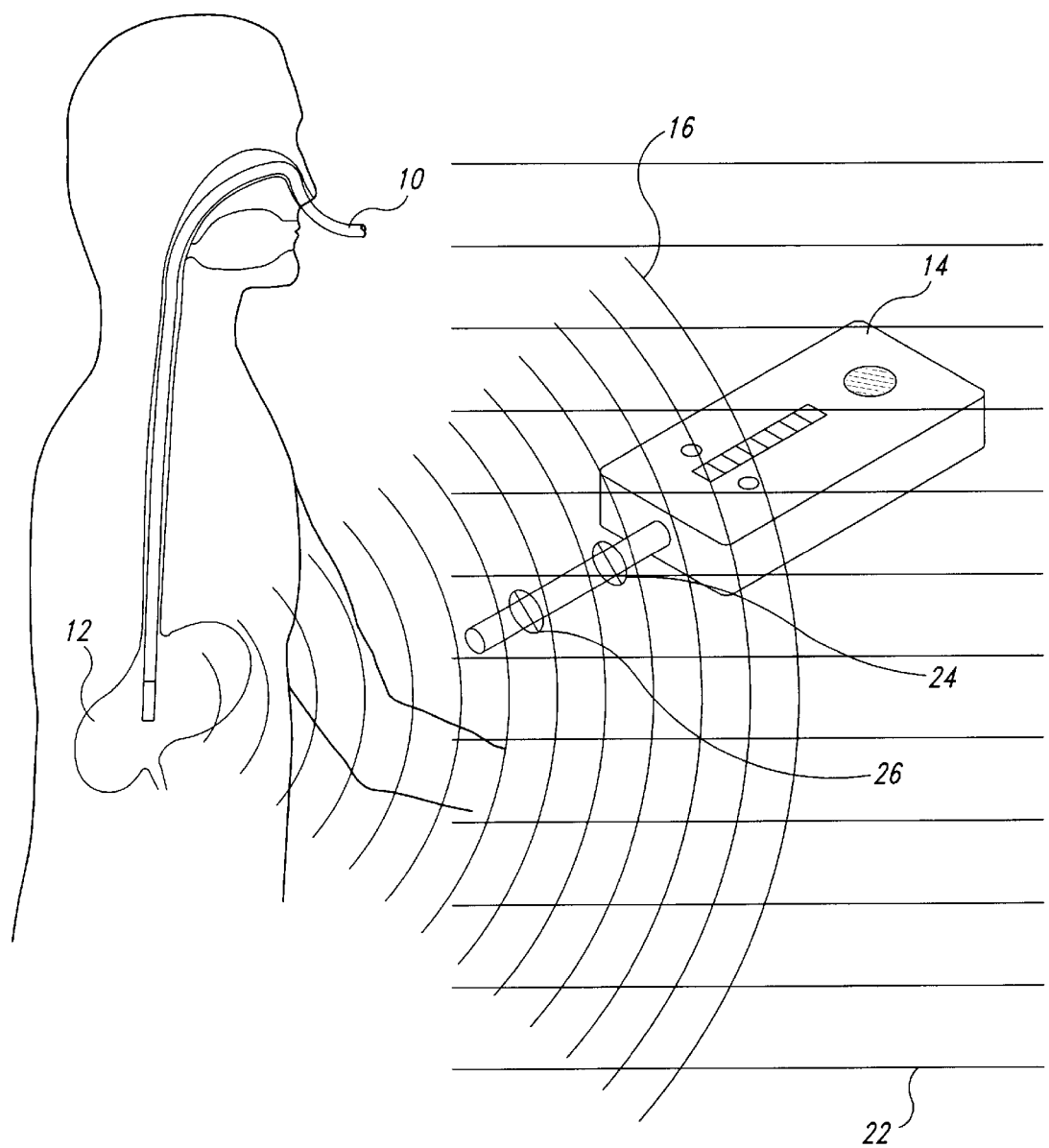
FIG. 1 illustrates the location of a magnet fixed to the end of a medical tube positioned within the body of a human patient using a known detection apparatus.
Figure 1:
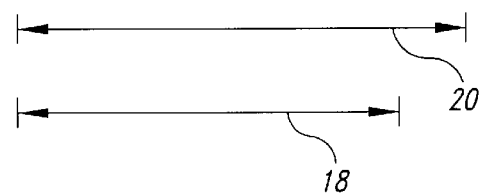

One known technique for locating a medical tube in the body of a patient is described in U.S. Pat. No. 5,425,382, which is incorporated herein by reference in its entirety. FIG. 1 illustrates the techniques described in U.S. Pat. No. 5,425,382. A tube 10, with a permanent magnet 12 located in its tip is inserted into the patient. In the example illustrated in FIG. 1, the tube 10 is a feeding tube that is inserted into the patient's nose, down the esophagus, and into the stomach. However, the system may be readily used with other types of tubes. A detection apparatus 14 is used to sense the magnet's static magnetic field strength 16 at two different distances 18 and 20 while immersed in the earth's ambient magnetic field 22. By measuring the static magnetic field strength 16 at two different distances 18 and 20, the detection apparatus 14 determines the magnetic field gradient. As the detection apparatus 14 is moved about the patient's body, greater and lesser magnetic field gradients are indicated. The tube 10 is located by moving the detection apparatus 14 until the greatest magnitude is indicated by the detection apparatus.

Figure 2:
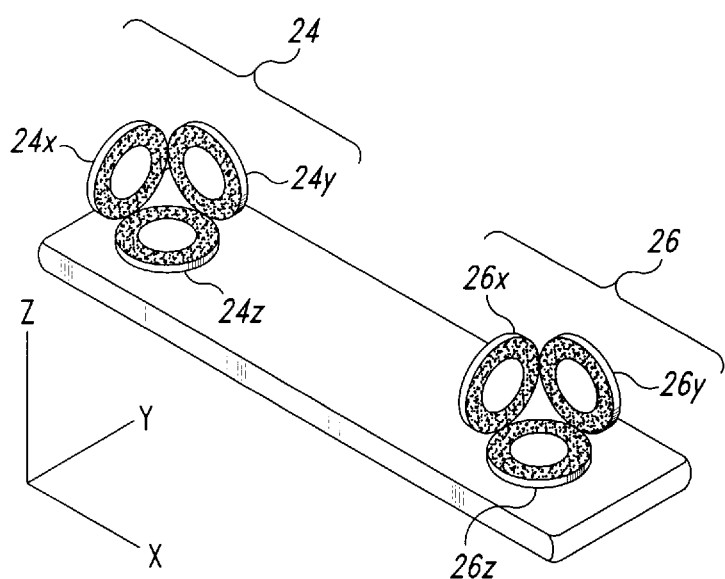
FIG. 2 illustrates the orientation of the x, y and z magnetic sensors used in a known detection apparatus.

The detection apparatus 14 described in U.S. Pat. No. 5,425,382 utilizes first and second magnetic sensors 24 and 26, respectively. As described in that patent, the magnetic sensors 24 and 26 may each comprise flux-gate toroidal sensors to detect the magnetic field gradient. An alternative magnetic field gradient detector system is described in presently pending U.S. application Ser. No. 08/644,446, filed on May 2, 1996, and which is incorporated herein by reference in its entirety. FIG. 2 illustrates the magnetic sensor arrangement described in the above-referenced application. The magnetic sensors 24 and 26 each comprise three orthogonally arranged flux-gate toroidal sensor elements. The magnetic sensor 24 comprises magnetic sensor elements 24x, 24y, and 24z that are orthogonally arranged to measure magnetic field strength in three orthogonal directions, illustrated in FIG. 2 by x, y, and z axes, respectively. Similarly, the magnetic sensor 26 comprises magnetic sensor elements 26x, 26y, and 26z to measure magnetic field strength in the x, y, and z directions, respectively. Using the sensors 24 and 26, the magnetic field gradient may be determined in the x, y, and z directions. With measurements of magnetic field gradient in three directions, the location of the magnet 12 (see FIG. 1) may be readily determined using conventional vector mathematics. The mathematical sign of the magnetic gradient is indicative of the direction of the magnetic field dipole of the magnet 12.

The magnet, and hence the medical tube, is detected using a known detection apparatus that contains at least two static magnetic field strength sensors configured geometrically to null detection of ambient, homogeneous magnetic fields (e.g., the earth's field), while still detecting the magnetic field strength gradient produced by the magnet.

The magnet detection apparatus illustrated in FIGS. 1 and 2 detects the location of the magnet based on the difference in magnetic field strength at the two sensors. However, it is possible to construct a magnetic field detection apparatus with different sensor configurations to provide additional data related to the position and orientation of the magnet. The present invention is directed to a technique for detection of a magnet using a multisensor array and a convergence algorithm that can accurately locate the position of the magnet in three dimensions. An exemplary embodiment of the invention is embodied in a detector system 100, shown in FIG. 3A. The detector system 100 includes a housing 102, control switches 104 such as a power switch and a reset switch, and a display 106. In an exemplary embodiment, the display 106 is a two-dimensional liquid crystal display. The display 106 may have an opaque background, or have a transparent area which allows the caregiver to view the skin below the surface of the detector system 100.

Figure 3A:
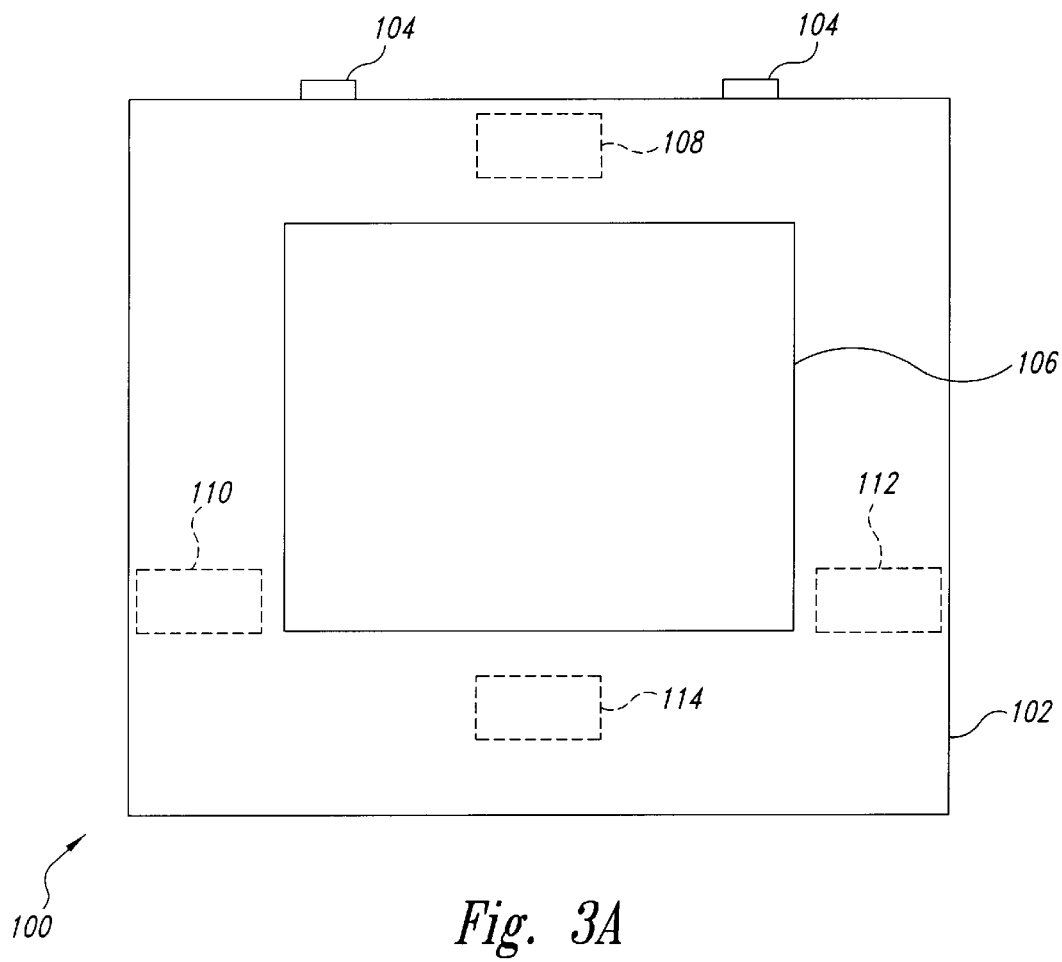
FIG. 3A is a top plan view of the detector of the present invention illustrating one possible arrangement of magnetic sensors.
Figure 3B:
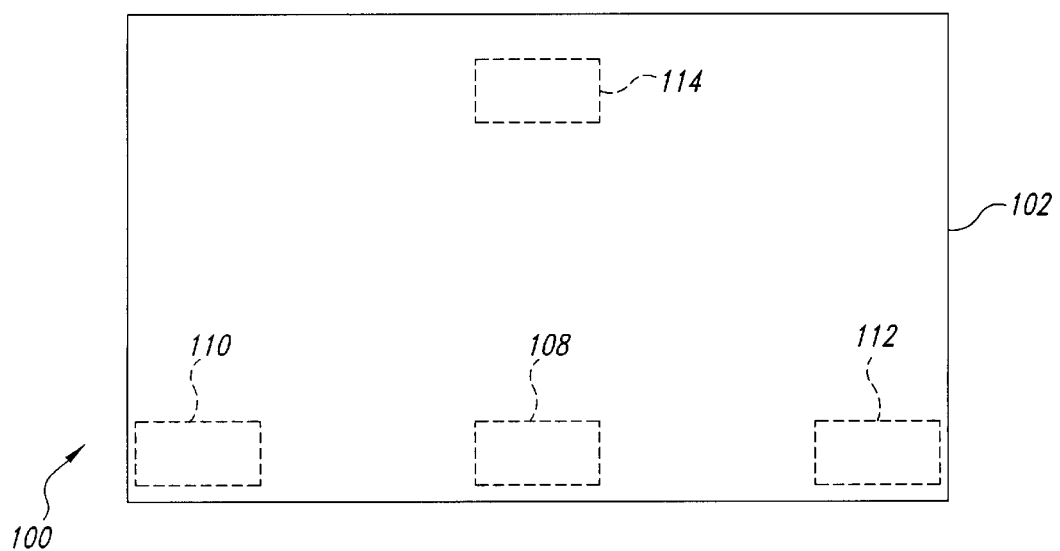
FIG. 3B is a side view of the detector of FIG. 3A.

Also mounted within the housing 102 are first, second, third, and fourth magnetic sensors 108, 110, 112, and 114, respectively. In a preferred embodiment, the magnetic sensors 108–112 are spaced to provide maximal separation within the housing 102. In an exemplary embodiment, the first, second, and third magnetic sensors 108–112 are arranged in a substantially planar fashion within the housing 102, as illustrated in FIG. 3B. The fourth magnetic sensor 114 is also mounted within the housing 102, but not in the plane formed by the first, second, and third magnetic sensors 108–112. In an exemplary embodiment, the fourth magnetic sensor 114 is positioned so as to form a tetrahedral arrangement with respect to the magnetic sensors 108–112.

Figure 4:
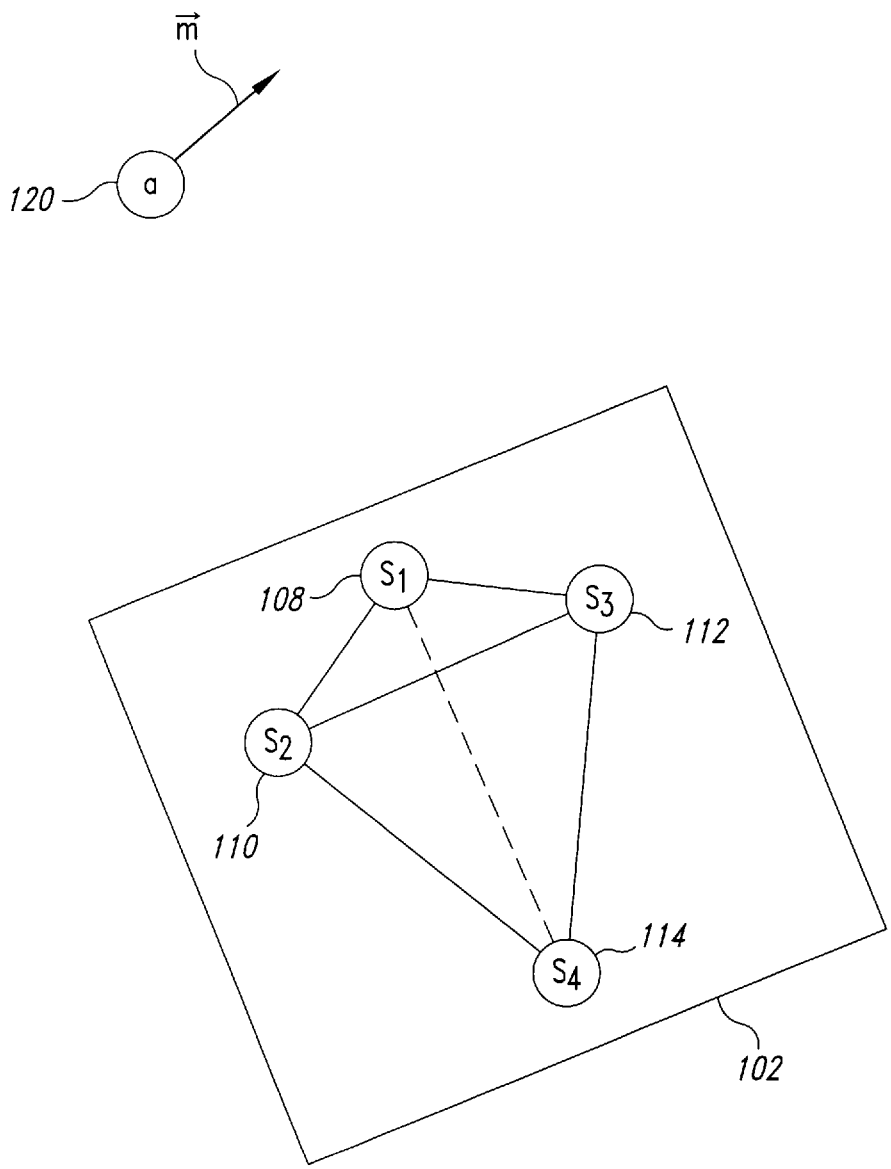
FIG. 4 illustrates the generation of magnetic field strength vectors using the magnetic sensor configuration of FIG. 3 to determine the location of a magnet.

This is best illustrated in FIG. 4 where the magnetic sensors 108–114 are positioned at locations $S_1$ to $S_4$, respectively, to define the corners of a tetrahedron. Although the system 100 described in FIGS. 3A, 3B, and 4 illustrates a tetrahedral configuration for the magnetic sensors 108–114, the principles of the present invention are readily applicable to any multisensor array. Accordingly, the present invention is not limited by the specific physical arrangement of the magnetic sensors. In an exemplary embodiment, each of the magnetic sensors 108–114 comprise three independent magnetic sensing elements orthogonally arranged to provide three-dimensional measurement in the x, y, and z directions, such as illustrated in FIG. 2. The magnetic sensors 108–114 are aligned with respect to a common origin such that each magnetic sensor senses the magnetic field in the same x, y and z directions. This permits the detection of magnetic field strength in a three-dimensional space by each of the magnetic sensors 108–114. The arrangement of the magnetic sensors 108–114 permits the detection of a magnet in a three-dimensional space within the patient. That is, in addition to locating the magnet within the patient, the detector system 100 provides depth information.

The mathematical description provided below may be most easily understood with respect to a Cartesian coordinate system using magnetic sensing elements orthogonally arranged in the x, y, and z directions. However, it should be clearly understood that the present invention is not limited to such an arrangement. Any alignment of the magnetic sensing elements may be used with the detector system 100 so long as the location and orientation of the magnetic sensors 108–114 are known. Therefore, the present invention is not limited by the specific configuration of magnetic sensing elements.

As illustrated in FIG. 4, a magnet 120 is positioned at a location a. As is known in the art, the magnet 120 has a magnetic dipole that is represented by the vector m. The vector m represents the strength and orientation of the magnetic dipole. Under ideal conditions, the magnetic sensors 108–114 can locate the magnet 120 at location a with a single measurement. However, the presence of the earth's magnetic field, stray magnetic fields that may be present near the vicinity of the magnet 120, internal noise from the magnet sensors 108–114, internal noise generated by electronics associated with the magnetic sensors, such as amplifiers and the like, make it virtually impossible to perform a measurement under "ideal" conditions. To provide accurate positional information for the magnet 120 in the presence of various forms of noise, the detector system 100 uses known formulas for magnetic field strength, plus actual sensor measurements as inputs to an estimation algorithm that converges to provide an accurate reading of the location and orientation of the magnet 120.

Figure 5:
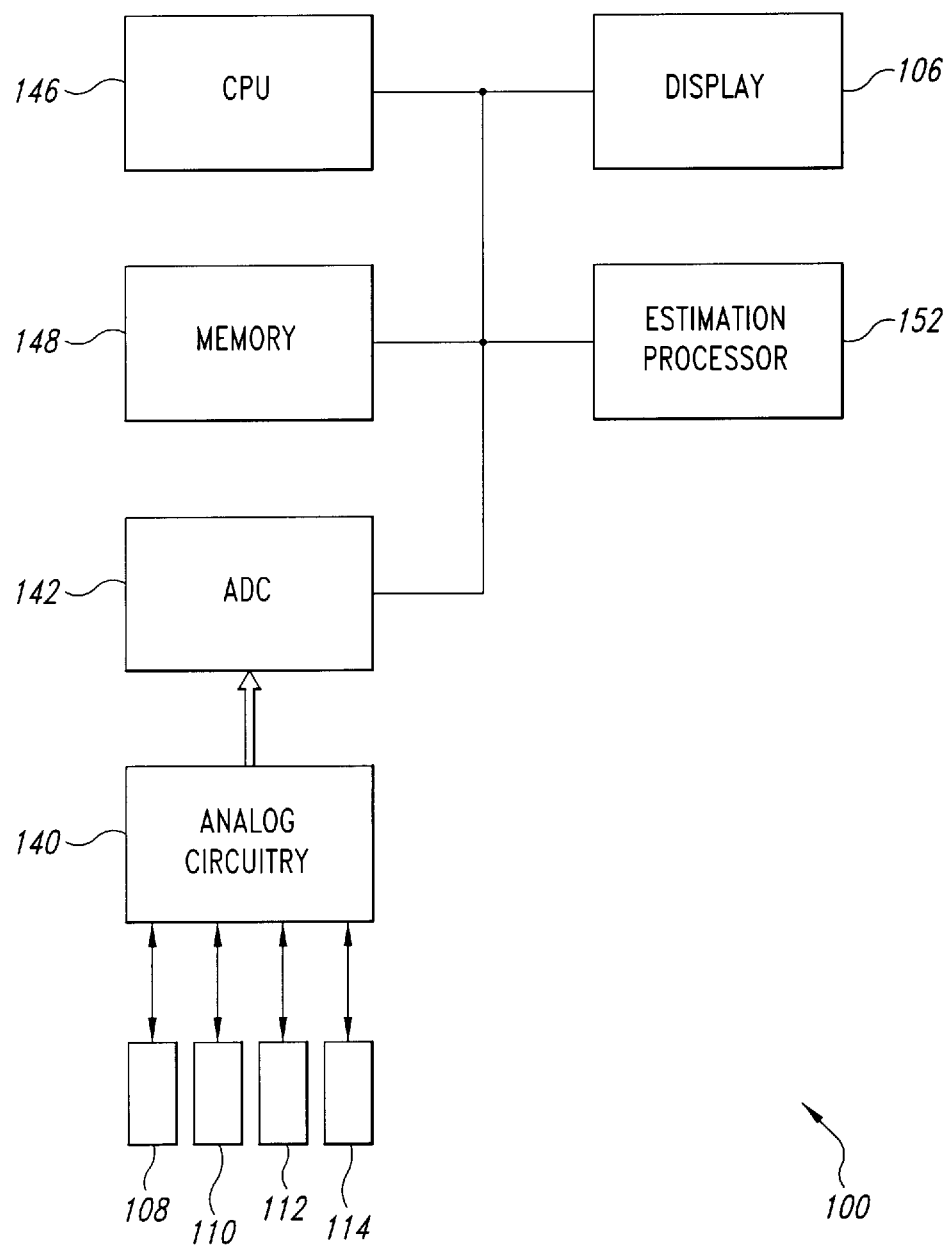
FIG. 5 is a functional block diagram of an exemplary embodiment of a system constructed in accordance with the present invention to determine the location of a magnet.

The elements used to process data from the magnetic sensor 108–114 are illustrated in a functional block diagram of FIG. 5 where the magnetic sensors 108–114 are coupled to analog circuitry 140. The specific form of the analog circuitry 140 depends on the specific form of the magnetic sensors 108–114. For example, if the magnetic sensors 108–114 are orthogonally positioned flux-gate toroidal sensors, similar to those illustrated in FIG. 2, the analog circuitry 140 may include amplifiers and integrators such as discussed in U.S. Pat. No. 5,425,382 and pending U.S. patent application Ser. No. 08/644,446, filed May 2, 1996. However, the magnetic sensors 108–114 may be any form of magnetic sensor. Several different types of magnetic sensors may be used in the practice of the present invention, including, but not limited to, Hall-effect, flux-gate, wound-core inductive, squid, magneto-resistive, nuclear precession sensors, and the like. Commercial magnetic field gradient sensors in the form of an integrated circuit can also be used with the detector system 100. Furthermore, the magnetic sensors 108–114 need not be identical types of sensors. For example, the magnetic sensors 108–112 may be one type of sensor while the magnetic sensor 114 may be a different type. The analog circuitry 140 is designed to operate with the specific form of the magnetic sensors 108–114. The specific design of the analog circuitry 140 is well within the knowledge of one of ordinary skill in the art and need not be described in greater detail herein.

The output of the analog circuitry 140 is coupled to an analog-to-digital converter (ADC) 142. The ADC 142 converts the analog output signals from the analog circuitry 140 to a digital form. The operation of the ADC 142 is well known to those of ordinary skill in the art and will not be described in detail herein. The detector system 100 also includes a central processing unit (CPU) 146 and a memory 148. In an exemplary embodiment, the CPU 146 is a microprocessor, such as a Pentium™ or the like. The memory 148 may include both read-only memory and random access memory. The various components, such as the ADC 142, CPU 146, memory 148, and display 106 are coupled together by a bus system 150. As can be appreciated by those of ordinary skill in the art, the bus system 150 illustrates a typical computer bus system and may carry power and control signals in addition to data.

Also illustrated in the functional block diagram of FIG. 5 is an estimation processor 152. Operational details of the estimation processor 152 are provided below. It should be noted that the estimation processor 152 is preferably implemented by computer instructions stored in the memory 148 and executed by the CPU 146. However, for the sake of clarity, the functional block diagram of FIG. 5 illustrates the estimation processor 152 as an independent block since it performs an independent function. Alternatively, the estimation processor 152 can be implemented by other conventional computer components, such as a digital signal processor (not shown).

As will be described in greater detail below, the estimation processor 152 performs an iterative comparison between an estimated position of the magnet 120 (see FIG. 2) and a measured position of the magnet 120 based on data derived from the magnetic sensors 108–114. The iterative process continues until the estimated position and the measured position converge, resulting in an accurate measurement of the location a (see FIG. 4) of the magnet 120.

The detector system 100 assumes that the magnetic sensors 108–114 are sufficiently far from the location a of the magnet 120 that the magnet may be treated as a point dipole source and that the spatial variation of any extraneous magnetic fields, such as the earth's magnetic field, is small compared to the inhomogeneity produced by the presence of the point dipole source.

The equations used by the estimation processor 152 are readily derived from the fundamental laws of physics related to electricity and magnetism. A magnetic field B produced by the magnetic dipole of a strength m, and situated at a location a, and measured at a location s is given by the following:

$$B(s) = \frac{3((s-a) \cdot m)(s-a) - \|s-a\|^2 m}{\|s-a\|^5} \quad (1)$$

where $\|s-a\|$ is a modulus value well known in matrix mathematics (e.g., $\|s-a\|^2$ is a square modulus). It should be noted that the values a, m, s, and B are all vector values.

Thus, a single one of the magnetic sensors 108–114 can be used to determine the strength of the magnetic field B at locations S1–S4, respectively. Changes in the magnetic field B over distance is defined as a gradient G(s) of B, which is a derivative of B with respect to s. The gradient G(s) can be represented by a 3×3 matrix derived from equation (1) and expressed in the following form:

$$G(s) = \frac{-(15((s-a) \cdot m))(s-a)(s-a)^T + 3\|s-a\|^2((s-a)m^T + m(s-a)^T + ((s-a) \cdot m)I)}{\|s-a\|^7} \quad (2)$$

where T is a matrix transpose and I is a 3×3 identity matrix having the following form:

$$I = \begin{bmatrix} 1 & 0 & 0 \\ 0 & 1 & 0 \\ 0 & 0 & 1 \end{bmatrix}$$

It should be noted that equation (1) could be solved directly for the value a given the values B, m, and s. However, such a calculation can be difficult to solve and may require significant computing power. The iterative estimation process described below determines the location a and orientation of the magnet 120 by estimating the location a and comparing a predicted magnetic field that would result from the magnet 120 being located at the estimated location with the measured magnetic field as measured by the magnetic sensors 108–114. The iterative process varies the estimated location in a controlled manner until the predicted magnetic field closely matches the measured magnetic field. At that point, the predicted location and orientation matches the actual location a and orientation of the magnet 120. Such an iterative process can be performed very quickly by the detector system 100 without the need for extensive computational calculations required to solve for the location a directly using equation (1). Equation (2), indicating the gradient G(s) is used by the estimation processor 152 (see FIG. 5) to determine the magnitude and a direction of error in the estimated location. Thus, equation (1) is used to generate predicted values and the error results are used in equation (2) to determine how to alter the estimated position of the magnet 120.

The magnetic field strength B is measured at each of the locations $S_1$–$S_4$ by the magnetic sensors 108–114, respectively. While only four magnetic sensors are illustrated in FIG. 3A to FIG. 5, the measurement may be generalized to n sensors such that each of the magnetic sensors provides a measurement of $B(s_i)$ at points $s_i$, where i=1 to n. The estimation processor 152 calculates quantities $\Delta_{ij}$ (measured)=$B(s_i)$–$B(s_j)$. This calculation provides a measure of the gradient from magnetic sensor i to magnetic sensor j and also cancels out the effects of the earth's magnetic field, which is constant (i.e., gradient=0) at the magnetic sensor i and the magnetic sensor j. The estimation processor 152 also calculates predicted values $\Delta_{ij}$ (predicted) from equation (1). The estimates for the values a and m are adjusted until the measured values $\Delta_{ij}$ (measured) and predicted values $\Delta_{ij}$ (predicted) match as closely as possible. For example, the detector system 100 may initially assume that the location a of the magnet 120 is centered under the housing 102. Based on this estimation, the estimation processor 152 calculates the predicted values for magnetic field strength at each of the magnetic sensors 108–114. In an exemplary embodiment, each of the magnetic sensors 108–114 provide a measure of the magnetic field B in three orthogonal directions resulting in magnetic field strength values $B_{xi}$, $B_{yi}$, and $B_{zi}$ where i equals 1 to n. Similarly, the gradient G(s) is also calculated for each of the three orthogonal directions.

The estimation processor 152 also uses measured magnetic field strength values from each of the magnetic sensors 108–114 and compares $\Delta_{ij}$ (predicted) with $\Delta_{ij}$ (measured). Based on the difference between $\Delta_{ij}$ (predicted) and $\Delta_{ij}$ (measured), the estimation processor 152 generates a new estimated location for the magnet 120 (see FIG. 4) and iterates the prediction process until $\Delta_{ij}$ (predicted) closely matches $\Delta_{ij}$ (measured).

If an estimated position of the magnet 120 (see FIG. 4) is calculated at an initial time as an initial estimation, a new estimated position may be readily calculated a short time later when the change in position and orientation of the magnet 120 will be small, thus facilitating real-time tracking of the magnet as the housing 102 is moved on the surface of the patient.

The degree of match between $\Delta_{ij}$ (predicted) and $\Delta_{ij}$ (measured) may be measured by a cost function comprising, for example, the sum of the squares of the difference between $\Delta_{ij}$ (predicted) and $\Delta_{ij}$ (measured) and then using non-linear iterative optimization algorithms to minimize the value of the cost function. The required gradients of the cost function are calculated using equation (2) above. Many different, well-known optimization techniques, such as gradient-based methods, simulated annealing, neural networks, simplex methods, etc. neural networks, may be used by the estimation processor 152 to achieve the desired degree of match between $\Delta_{ij}$ (predicted) and $\Delta_{ij}$ (measured).

Figure 6:
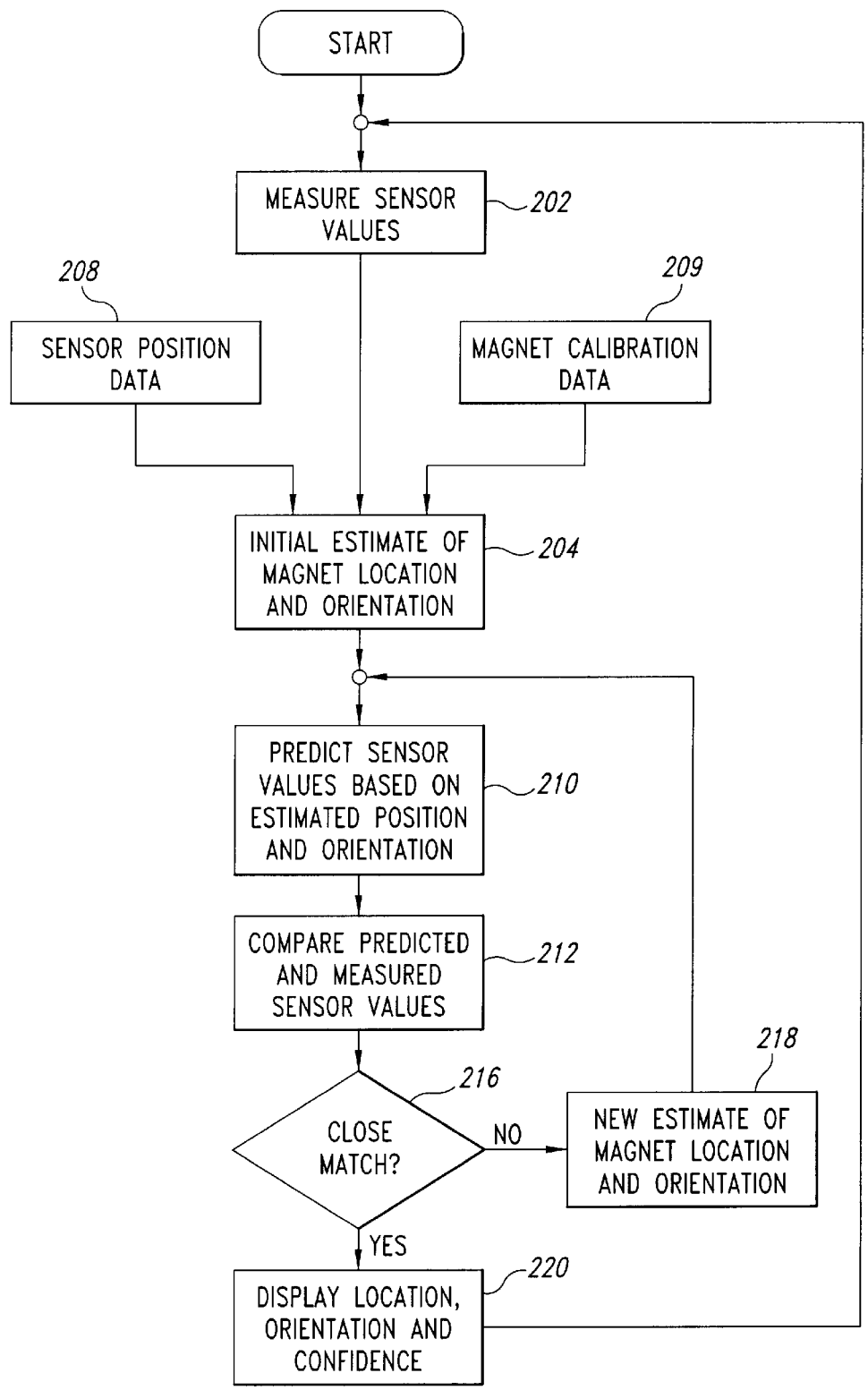
FIG. 6 is a flowchart used by the system of FIG. 5 to determine the location of a magnet.

The operation of the detector system 100 is illustrated in the flowchart of FIG. 6. At a start 200 the magnet 120 (see FIG. 4) has been inserted into the patient. In step 202, the detector system 100 measures sensor values from the magnetic sensors 108–114. In step 204, the estimation processor 152 (see FIG. 5) calculates an initial estimate of the location a and orientation of the magnet 120. The initial estimate includes sensor position data from step 208 and magnet calibration data from step 209. The sensor position data calculated in step 208 provides data relating the position of each of the magnetic sensors 108–114 relative to a selected origin. For example, one magnetic sensor (e.g., magnetic sensor 108) may be arbitrarily selected as the mathematical origin for purposes of determining the relative positions of the other magnetic sensors (e.g., magnetic sensors 110–114). The common origin provides a frame of reference for purposes of the mathematical calculations. As previously discussed, the magnetic sensors 108–114 are aligned with respect to the common origin so that each magnetic sensor measures the magnetic field in the same x, y, and z directions. As those of ordinary skill in the art can appreciate, any selected origin can be used satisfactorily with the detector system 100.

The magnetic calibration data derived in step 209 is typically provided by the magnet manufacturer and includes data related to the strength of the magnetic dipole m (see FIG. 4), as well as the size and shape of the magnet 120. The measured sensor values, sensor position data, and magnet calibration data are provided as inputs to the estimation processor 152 (see FIG. 5) in step 204.

In step 210, the estimation processor 152 (see FIG. 5) calculates predicted sensor values. As described above, this requires a measurement $\Delta_{ij}$ (predicted) for each combination of the magnetic sensors 108–114 in each of the three orthogonal directions x, y, and z. In step 212, the estimation processor 152 compares the predicted sensor values (i.e., $\Delta_{ij}$ (predicted)) with the measured sensor values (i.e., $\Delta_{ij}$ (measured)). In decision 216, the estimation processor 152 determines whether the predicted and measured sensor values match within a desired degree of tolerance. If the predicted sensor values and the measured sensor values are not a close match, the result of decision 216 is NO. In that event, the estimation processor 152 calculates a new estimate of the magnet location a and orientation in step 218. Following the calculation of a new estimated location a of the magnet 120, the estimation processor 152 returns to step 210 to calculate a new set of predicted sensor values using the new estimate of magnet location and orientation. The estimation processor 152 continues this iterative process of adjusting the estimated location a of the magnet 120 and orientation and comparing predicted sensor values with measured sensor values until a close match is achieved. When a close match between the predicted sensor values and the measured sensor values is achieved, the result of decision 216 is YES. In that event, in step 220 the detector system 100 displays the magnet location a and orientation on the display 106 (see FIGS. 3A, 3B, and 4). In addition, the detector system 100 may display a confidence value indicative of a degree of confidence with which the location a and orientation of the magnet 120 have been determined. The calculation of a confidence value based on statistical data is well known in the art and need not be described in detail herein. Following the display of location and orientation data in step 220, the detector system 100 returns to step 202 and repeats the process on a new set of measured sensor values. If cost function is too high, a close match may not be achieved in decision 216. Such conditions may occur, for example, in the presence of extraneous magnetic fields. In practice, it has been determined that close matches have a cost function in the range of 1–2 while the minimum cost function for an inaccurate local minima are orders of magnitude greater. If a close match cannot be achieved, (i.e., the cost function is too great), the detector system 100 can start the measurement process anew with a new estimated location or generate an error message indicating an unacceptably high cost function.

The iterative estimation process is described above using the difference in magnetic strength B provided by different pairs of magnetic sensors 108–114. Alternatively, the detector system 100 can use the measured field gradient values G. In this embodiment, equation (2) may be fit to the measured values, in a manner as described above with respect to the iterative process to fit the measurements of B. With respect to the flowchart of FIG. 6, the step 202 provides gradient values with respect to pairs of the magnetic sensors 108–114. For example, a magnetic gradient measurement can be calculated using the magnetic field B measured by the magnetic sensor 114 with respect to the magnetic field measured by each of the remaining magnetic sensors 108–112, respectively. In step 204, the estimation processor 152 determines an initial estimate of the magnet location and orientation, and, in step 210, calculates predicted sensor values using equation (2). In step 212, the measured sensor values are compared with the predicted sensor values using conventional techniques, such as the cost functions described above. The iterative process continues until the measured sensor values and the predicted sensor values match within the predetermined degree of tolerance.

In yet another alternative technique, the detector system 100 utilizes the measurement data and solves equation (2) for a directly. The direct solution approach utilizes the fact that G is a symmetric matrix with positive eigenvalues. The eigenvalues and eigenvectors of the matrix G may be calculated and used algebraically to solve for the location a and m directly. This assumes that the magnitude, but not the direction, of m is known. In practice, the magnitude m is known because magnet calibration data is provided by the manufacturer. It should be noted that this technique requires an additional magnetic sensor to determine the orientation of the magnetic dipole. Mathematically, the orientation of the magnetic dipole is indicated by a + or − sign. The additional magnetic sensor, which need only measure the magnetic field strength B, is used to determine the sign of the mathematical function. In addition, combinations of these various techniques may be used by the detector system 100 to determine the location a of the magnet 120.

In yet another alternative, a Kalman filter may be used with equations (1) and (2) above to track the position of the magnetic dipole m with respect to the multi-detector array formed by the magnetic sensors 108–114. As is known to those of ordinary skill in the art, Kalman filters are statistical predictive filters that use statistical signal processing and optimal estimation. Numerous textbooks, such as "Tracking And Data Association," by Y. Bar-Shalom and R. E. Fortmann, Academic Press, Boston, 1988, provide details on the theory and operation of Kalman filters. In addition to the individual techniques described above, it is possible to use any or all of these techniques in a combination, such as a sum of cost functions for each sensor type. For example, the differences between $\Delta_{ij}$ (predicted) and $\Delta_{ij}$ (measured) can be required to match within a certain tolerance. If the multiple mathematical techniques are unable to identify a solution for which all difference values meet that tolerance, then an error can be signaled to the operator using the display 106 (see FIG. 5). Assuming the errors in each sensor measurement are independent and small, the uncertainty in the estimate of the location a can be calculated using, for example, Cramer-Rao bounds. Thus, a degree of redundancy between measurement techniques can be advantageously implemented by the detector system 100. Such redundancy is highly desirable for biomedical applications.

FIG. 3A illustrates the operation of the detector system 100 for a specific configuration of the magnetic sensors 108–114. However, the techniques described above may be generalized to virtually any fixed configuration of sensors. A minimum of one gradient sensor or eight magnetic field sensors is required to measure G(s) and B(s), respectively, assuming that the strength of the magnetic dipole m is known. The magnetic sensors can be configured relatively arbitrarily and thus may be readily positioned at locations within the housing 102 (see FIGS. 3A and 3B) based on instrument design and/or other signal or noise considerations.

The magnetic sensors 108–114 may be calibrated using the known strength of the earth's magnetic field. In the absence of any inhomogeneous fields (i.e., away from any strong magnetic dipoles) the X sensor element of all sensors 108–114 can be read at the same time. Similarly, all Y sensor elements and Z sensor elements can be read at the same time. In any configuration, the sum of the squares of the average readings of the magnetic field strength for each orthogonal direction (i.e., $B_x$, $B_y$, and $B_z$) should be constant. The constant value of the earth's magnetic field can be used to determine the appropriate calibration factors for each magnetic sensor using conventional algebraic and least squares fitting methods.

An alternative calibration technique uses a small magnet of known strength placed in one or more locations relative to the magnetic sensors 108–114. Measurements are performed at each of the one or more locations to determine the appropriate calibration factors for each magnetic sensor. Other techniques, such as the use of an electromagnetic cage, Helmholtz cage, or the like, may also be used to calibrate the magnetic sensors 108–114.

The display 106 (see FIG. 3A) provides graphical display of the position of the magnet 120 with respect to the housing 102. FIGS. 7A to 7D illustrate some of the different techniques used by the detector system 100 to indicate the location a of the magnet 120 (see FIG. 4). In the embodiment illustrated in FIG. 7A, the display 106 uses a circle 250 and a pair of orthogonal lines 252a and 252b to indicate the location a of the magnet 120 relative to the housing 102. The orthogonal lines 252a and 252b provide a visual indicator to the caregiver to assist in determining when the magnet 120 is centered under the detector system 100.

Figure 7A:
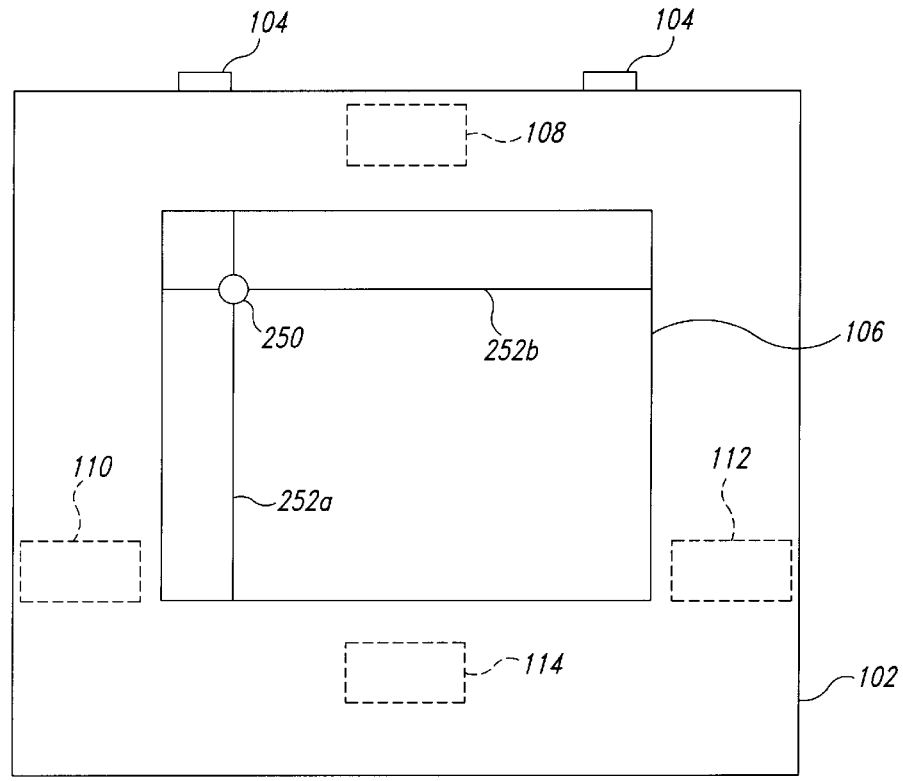
FIG. 7A illustrates one embodiment of the visual display used by the detector of FIG. 3A.
Figure 7B:
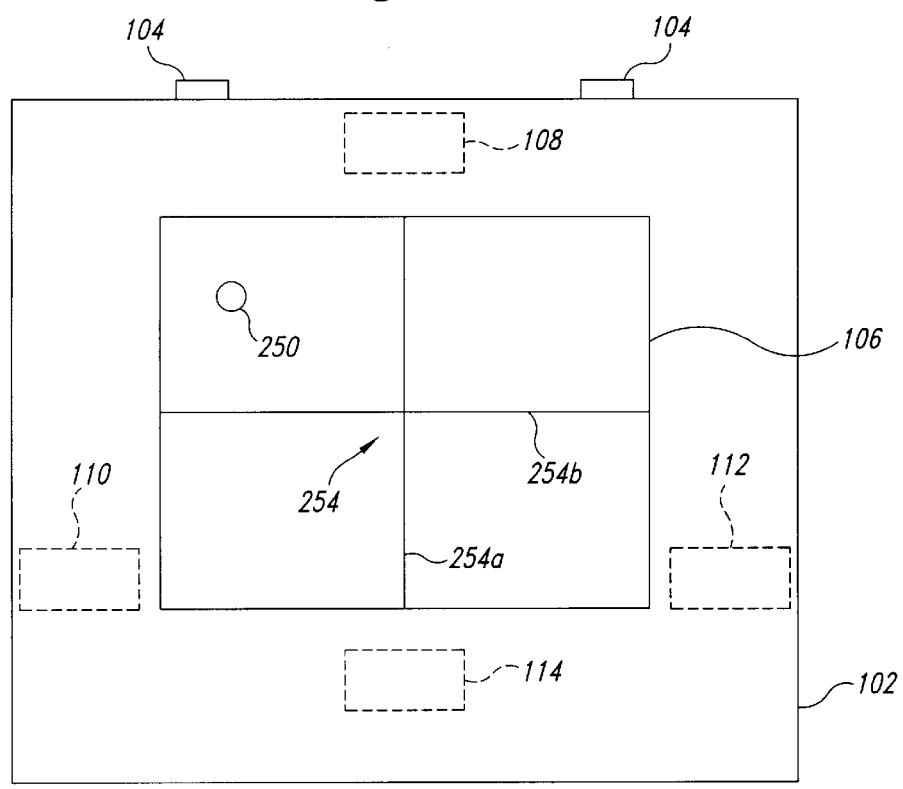
FIG. 7B is an alternative embodiment of the indicator used with the detector of FIG. 3A.

In an alternative embodiment, illustrated in FIG. 7B, a fixed indicator 254, such as orthogonal lines 254a and 254b, form cross-hairs over the center of the display 106. The circle 250, or other indicator, is used to provide a visual indication of the location a of the magnet 120 relative to the housing 102. The circle 250 is centered in the cross-hairs in the center of the display 106 when the magnet 120 is centered directly beneath the detector system 100.

Figure 7C:
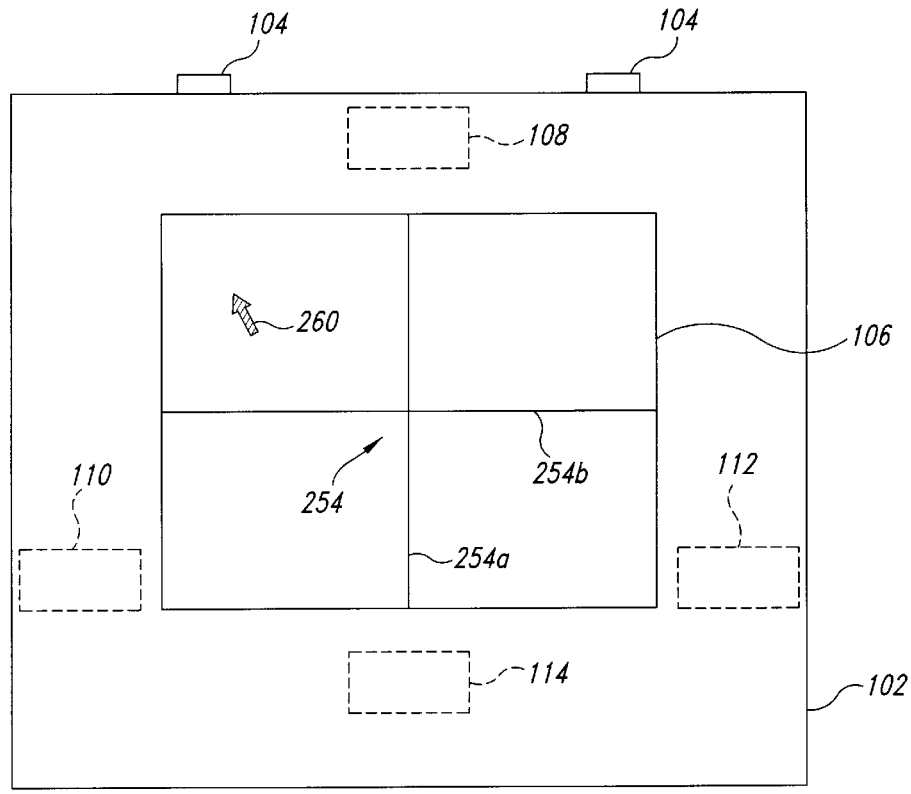
FIG. 7C is yet another alternative embodiment of the display used with the detector of FIG. 3A.

In yet another embodiment, shown in FIG. 7C, the display 106 provides a different indicator, such as an arrow 260, to provide a visual indication of the location a of the magnet 120. The arrow 260 may also be used to indicate the orientation of the magnet 120.

Figure 7D:
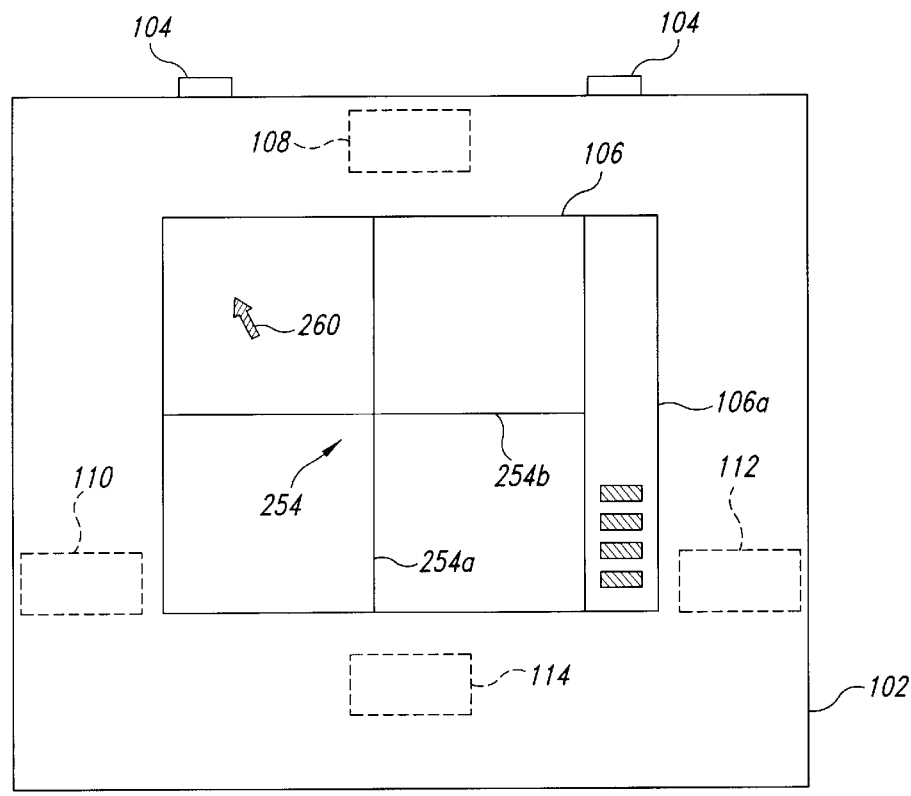
FIG. 7D is yet another alternative embodiment of the display of the detector of FIG. 3A with a depth indicator indicating the distance of the magnet from the detector.

The depth of the magnet 120 beneath the surface of the patient can be indicated on the display 106 in a variety of fashions. For example, a portion 106a of the display 106 can provide a visual indication of the depth of the magnet 120 using a bar graph, such as illustrated in FIG. 7D. However, the depth indicator portion 106a of the display 106 can also provide a numerical read-out of the depth of the magnet 106 in absolute units, such as centimeters, or in relative units.

Thus, the detector system 100 determines the location a of the magnet 120 in a three-dimensional space and provides an easy-to-read visual indication of the location of the magnet, including a depth indication, as well as the orientation of the magnetic dipole. While the housing 102 is illustrated as a rectangular housing, with the magnetic sensors 108–114 distributed equidistantly within the housing 102, the rectangular shape was chosen for its ease in grasping by the caregiver. However, the housing 102 can have any shape or size. Furthermore, the display 106, while illustrated as a liquid crystal display, can be any convenient two-dimensional display, such as a dot matrix display or the like. Thus, the present invention is not limited by the specific size or shape of the housing 102 or by the specific type of display 102. In addition, the detector system 100 can operate satisfactorily with a variety of different magnetic sensors. Thus, the present invention is not limited by the specific number or type of magnetic sensors employed in the detector system 100.

From the foregoing, it will be appreciated that, although specific embodiments of this invention have been described herein for purposes of illustration, various modifications may be made without deviating from the spirit and scope of the invention. Accordingly, the invention is not limited except by the appended claims.

What is claimed is:

1. A system for detecting a position of a magnet associated with an indwelling medical device from a measurement location on the surface of a patient and in the presence of a magnetic field of the Earth, the system comprising:

a housing;

first, second, and third magnetic sensors mounted in the housing, the first sensor positioned at a first distance from a magnet and generating a first set of electrical signals as a function of a first magnetic field strength and direction due to the magnet, the second sensor positioned at a second distance from the magnet and generating a second set of electrical signals as a function of a second magnetic field strength and direction due to the magnet, and the third sensor positioned at a third distance from the magnet and generating a third set of electrical signals as a function of a third magnetic field strength and direction due to the magnet;

a processor to calculate an estimated position of the magnet in a three-dimensional space and to calculate a predicted magnetic field strength for the first, second and third sensors based on the estimated position and to calculate a measured magnetic field strength using the first, second, and third sets of electrical signals wherein the processor generates the measured magnetic field strength by subtracting a first selected one of the first, second, and third sets of electrical signals from a second selected one of the first, second, and third sets of electrical signals different from the first selected one of the first, second, and third sets of electrical signals to cancel the effects of the Earth's magnetic field, the processor generating an error function based on a difference between the predicted magnetic field strength and the measured magnetic field strength; and a display providing a visual display of the three-dimensional position of the magnet using the error function.

2. The system of claim 1 wherein the processor iteratively calculates the estimated position and the predicted magnetic field strength until the error function indicates that the predicted magnetic field strength matches the measured magnetic field strength within a predetermined tolerance.

3. The system of claim 1 wherein the display provides the visual display based on a single generation of the error function.

4. The system of claim 1 wherein the processor calculates the estimated position using a mathematical equation representative of the magnetic field strength.

5. The system of claim 1 wherein the display has a two-dimensional display area indicating the position of the magnet with respect to the housing, and a depth indicator display area to indicate the distance of the magnet from the housing.

6. A system for detecting a position of a magnet associated with an indwelling medical device from a measurement location on the surface of a patient, the system comprising:

a housing;

first, second, and third magnetic sensors mounted in the housing, the first sensor positioned at a first distance from a magnet and generating a first set of electrical signals as a function of a first magnetic field strength and direction due to the magnet, the second sensor positioned at a second distance from the magnet and generating a second set of electrical signals as a function of a second magnetic field strength and direction due to the magnet, and the third sensor positioned at a third distance from the magnet and generating a third set of electrical signals as a function of a third magnetic field strength and direction due to the magnet;

a processor to calculate an estimated position of the magnet in a three-dimensional space and to calculate a predicted magnetic field strength for the first, second and third sensors based on the estimated position and to calculate a measured magnetic field strength using the first, second, and third sets of electrical signals, the processor generating an error function based on a difference between the predicted magnetic field strength and the measured magnetic field strength; and a two-dimensional display providing a visual display of the three-dimensional position of the magnet using the error function wherein at least a portion of the display is transparent to allow the user to view the surface of the patient beneath the transparent portion.

7. The system of claim 6 wherein the display includes a first visual indicator substantially centered in the two-dimensional display area and a second visual indicator indicating the position of the magnet with respect to the housing, the first visual indicator being a cross-hairs.

8. The system of claim 1 wherein the first, second, and third sensors are selected from a group of magnetic sensors comprising Hall-effect sensors, flux-gate sensors, wound-core inductive sensors, magnetic field gradient sensors, squid sensors, magneto-resistive sensors, and nuclear precession sensors.

9. The system of claim 1 wherein the magnet has a magnetic dipole moment indicative of an orientation of the magnet and the first, second, and third sensors detect the magnetic dipole moment.

10. The system of claim 9 wherein the detected magnetic dipole moment is displayed on the display to indicate the magnet orientation.

11. The system of claim 1 wherein each of the first, second, and third sensors comprises first, second, and third sensor elements arranged in an orthogonal fashion to detect magnetic field strength in three dimensions corresponding to the first, second, and third orthogonally arranged sensor elements, respectively.

12. The system of claim 1, further including a calibration circuit to calibrate said first, second, and third magnetic sensors.

13. The system of claim 1 wherein the processor generates a minimum value for the error function when analyzing the difference between the predicted magnetic field strength and the measured magnetic field, the processor further analyzing the minimum value for the error function with a predetermined minimum value and generating a signal to the user to indicate whether the minimum value is above or below the predetermined minimum value.

14. A system for detecting a position of a magnet associated with an indwelling medical device from a measurement location on the surface of a patient, the system comprising:

a plurality of magnetic sensors, each generating a set of electrical signals as a function of a magnetic field strength and direction due to a magnet;

a processor to calculate an estimated position of the magnet in a three-dimensional space and to calculate a predicted value related to the magnetic field strength for the plurality of sensors based on the estimated position and to calculate a measured value related to the magnetic field strength using the sets of electrical signals, the processor calculating the position of the magnet based on the predicted value related to magnetic field strength and the measured value related to magnetic field strength wherein the processor calculates a cost function based on a difference between the predicted value related to magnetic field strength and the measured value related to magnetic field strength, the processor further generating a minimum value for the cost function and analyzing the minimum value for the cost function with a predetermined minimum value, and generating a signal to the user to indicate whether the minimum value is above or below the predetermined minimum value; and a display providing a visual display of data relating to the position of the magnet.

15. The system of claim 14 wherein the processor iteratively calculates the estimated position and the predicted value related to the magnetic field strength until the predicted value related to the magnetic field strength matches the measured value related to the magnetic field strength within a predetermined tolerance.

16. The system of claim 15 wherein the processor calculates the position of the magnet based on a single calculation of the predicted value related to magnetic field strength.

17. The system of claim 14 wherein the processor calculates the estimated position using a mathematical equation representative of the magnetic field strength.

18. The system of claim 14 wherein the processor calculates the estimated position using a mathematical equation representative of a gradient of the magnetic field strength.

19. The system of claim 14 wherein each of the plurality of sensors comprises first, second and third sensor elements arranged in an orthogonal fashion to detect magnetic field strength in three dimensions corresponding to the first, second, and third orthogonally arranged sensor elements, respectively.

20. The system of claim 14 wherein the sensor elements are selected from a group of magnetic sensors comprising Hall-effect sensors, flux-gate sensors, wound-core inductive sensors, magnetic field gradient sensors, squid sensors, magneto-resistive sensors, and nuclear precession sensors.

21. The system of claim 14 wherein the display has a two-dimensional display area indicating the position of the magnet with respect to the housing, and a depth indicator display area to indicate the distance of the magnetic from the housing.

22. The system of claim 14 wherein the magnet has a magnetic dipole moment indicative of an orientation of the magnet and the sets of electrical signals generated by plurality of sensors are indicative of the magnetic dipole moment.

23. The system of claim 22 wherein the detected magnetic dipole moment is displayed on the display to indicate the magnet orientation.

24. The system of claim 14, further including a calibration circuit to calibrate said plurality of magnetic sensors.

25. A system for detecting a position of an indwelling medical device from a measurement location on the surface of a patient and in the presence of a magnetic field of the Earth, the system comprising:

a medical device suitable for insertion into the patient, the medical device having a magnet associated therewith;

a housing;

first, second, and third magnetic sensors mounted in the housing, the first sensor positioned at a first distance from the magnet and generating a first set of electrical signals as a function of a first magnetic field strength and direction due to the magnet, the second sensor positioned at a second distance from the magnet and generating a second set of electrical signals as a function of a second magnetic field strength and direction due to the magnet, and the third sensor positioned at a third distance from the magnet and generating a third set of electrical signals as a function of a third magnetic field strength and direction due to the magnet;

a processor to calculate an estimated position of the magnet in a three-dimensional space and to calculate a predicted magnetic field strength for the first, second and third sensors based on the estimated position and to calculate a measured magnetic field strength using the first, second, and third sets of electrical signals wherein the processor generates the measured magnetic field strength by subtracting a first selected one of the first, second, and third sets of electrical signals from a second selected one of the first, second, and third sets of electrical signals different from the first selected one of the first, second, and third sets of electrical signals to cancel the effects of the Earth's magnetic field, the processor generating an error function based on a difference between the predicted magnetic field strength and the measured magnetic field strength; and a display to indicate the position of the indwelling device by providing a visual display of the three-dimensional position of the associated magnet using the error function.

26. The system of claim 25 wherein the medical device is a catheter.

27. The system of claim 26 wherein the catheter is a feeding tube.

28. The system of claim 26 wherein the catheter is a vascular tube.

29. The system of claim 25 wherein the medical device is a guidewire.

30. The system of claim 25 wherein the medical device is a medical instrument.

* * * * *